United States Patent
Buchwald-Werner et al.

(10) Patent No.: US 10,596,212 B2
(45) Date of Patent: Mar. 24, 2020

(54) MANGIFERA INDICA AS A SIRTUIN 1 ACTIVATING AGENT

(71) Applicant: Vital Solutions Swiss AG, Basel (CH)

(72) Inventors: Sybille Buchwald-Werner, Dusseldorf (DE); Karin Berger Buter, Uttwil (CH)

(73) Assignee: VITAL SOLUTIONS SWISS AG, Basel (CH)

( * ) Notice: Subject to any disclaimer, the term of this patent is extended or adjusted under 35 U.S.C. 154(b) by 555 days.

(21) Appl. No.: 15/304,272

(22) PCT Filed: Apr. 16, 2015

(86) PCT No.: PCT/EP2015/058284
§ 371 (c)(1),
(2) Date: Oct. 14, 2016

(87) PCT Pub. No.: WO2015/158836
PCT Pub. Date: Oct. 22, 2015

(65) Prior Publication Data
US 2017/0042957 A1  Feb. 16, 2017

(30) Foreign Application Priority Data
Apr. 16, 2014 (EP) .................................. 14165035

(51) Int. Cl.
*A61K 36/22* (2006.01)
*A23L 33/105* (2016.01)
*C12N 9/16* (2006.01)

(52) U.S. Cl.
CPC ............ *A61K 36/22* (2013.01); *A23L 33/105* (2016.08); *A23V 2002/00* (2013.01); *C12N 9/16* (2013.01)

(58) Field of Classification Search
CPC .......... A23V 2002/00; A23V 2200/302; A23V 2250/21; A23L 33/105; A61K 36/22; C12N 9/16
See application file for complete search history.

(56) References Cited

U.S. PATENT DOCUMENTS

2012/0202755 A1   8/2012   Wang et al.

FOREIGN PATENT DOCUMENTS

CN        102813645 A     12/2012
WO          00/38699 A1    7/2000

OTHER PUBLICATIONS

Shah KA, et al "Mangifera Indica (Mango)" Pharmacogn Rev. Jan.-Jun. 2010; 4(7): 42-48; doi: 10.4103/0973-7847.65325: 10.4103/0973-7847.65325. (Year: 2010).*
Lucas EA, et al "Mango modulates body fat and plasma glucose and lipids in mice fed a high-fat diet" British Journal of Nutrition (2011), 106, 1495-1505; doi:10.1017/S0007114511002066. (Year: 2011).*
International Search Report and Written Opinion dated Jun. 8, 2015 from International Application No. PCT/EP2015/058284, pp. 1-13.
Jayasena et al., "The role of polyphenols in the modulation of sirtuins and other pathways involved in Alzheimer's disease", Ageing Research Rviews, vol. 12, No. 4, Jul. 5, 2013, pp. 867-883.
Miura et al., "The Suppressive Effect of Mangiferin with Exercise on Blood Lipids in Type 2 Diabetes", Biological & Pharmaceutical Bulletin (of Japan), vol. 24, No. 9, Sep. 1, 2001, pp. 1091-1092.
Liu et al., "Up-regualtion of glyoxalase 1 by mangiferin prevents diabetic nephropathy progression in streptozotocin-induced diabetic rats", European Journal of Pharmacology, vol. 721, No. 1, Sep. 10, 2013, pp. 355-364.
Ribeiro et al., "Phenolic compounds and antioxidant capacity of Brazilian mango (*Mangifera indica* L.) varieties", Food Chemistry, vol. 110, No. 3, Oct. 1, 2008, pp. 620-626.
Sebastian et al., "From Sirtuin Biology to Human Diseases: An Update", The Journal of Biological Chemistry, vol. 287, No. 51, Oct. 18, 2012, pp. 42444-42452.
National Biodiversity Authority, India, The Biological Diversity Act, 2002.†

* cited by examiner
† cited by third party

*Primary Examiner* — Aaron J Kosar
(74) *Attorney, Agent, or Firm* — MH2 Technology Law Group, LLP

(57) ABSTRACT

The invention relates to a *Mangifera* (Mango) *Indica* preparation as Sirtuin 1 activating agent for in vivo and in vitro applications. The preparation may be used to reduce the risk of developing obesity, type II diabetes, elevated blood lipid levels, artheriosclerosis and cardiovascular diseases, as well as a cell and DNA protector.

36 Claims, 1 Drawing Sheet

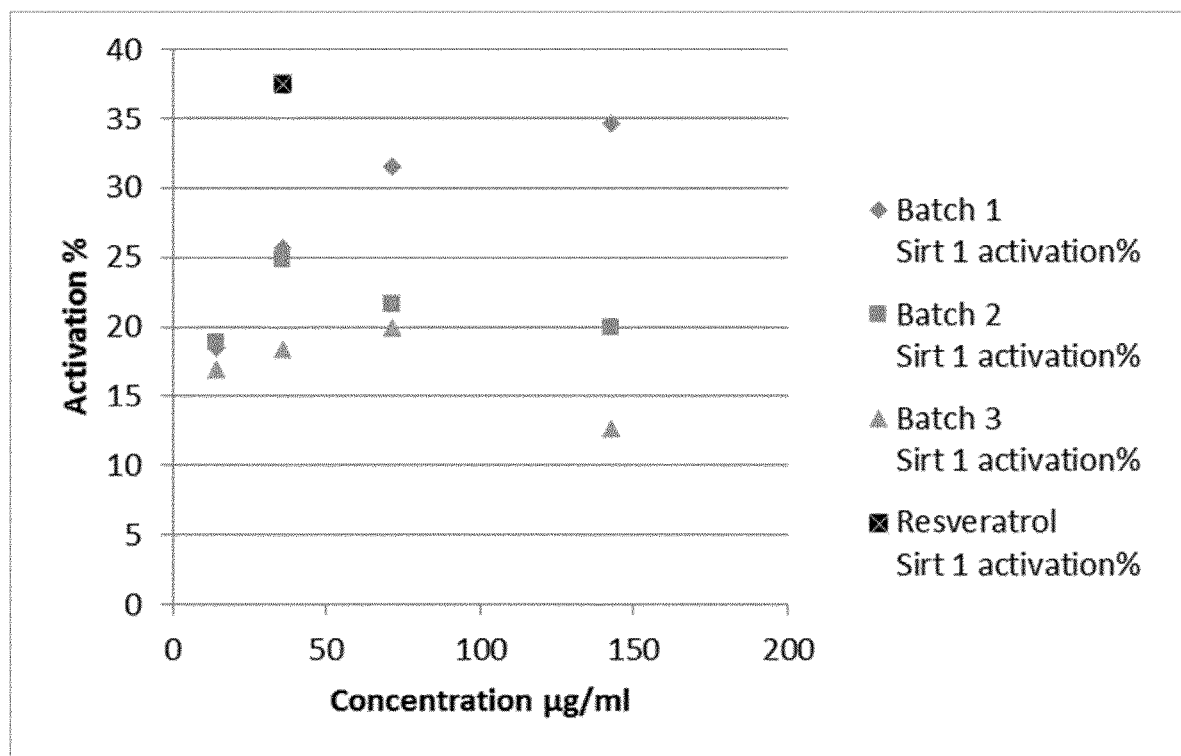

MANGIFERA INDICA AS A SIRTUIN 1 ACTIVATING AGENT

CROSS-REFERENCE TO RELATED APPLICATIONS

This application is a U.S. National Stage application of PCT/EP2015/058284 filed 16 Apr. 2015, which claims priority to European Application No. 14165035.8 filed 16 Apr. 2014, the entire disclosures of which are hereby incorporated by reference in their entireties.

TECHNICAL FIELD

The invention relates to food, a dietary supplement or a drug composition comprising a *Mangifera* (Mango) *indica* fruit preparation as Sirtuin 1 (SIRT1) activating agent and especially its beneficial effects to maintain or improve healthy body composition, healthy glucose, insulin and/or lipid metabolism, energy homeostasis, physical power, muscle mass, cell protection and thereby slowing down the aging process and preventing age related chronic diseases.

BACKGROUND OF THE INVENTION

Human aging is linked to structural and metabolic changes, which start already in the twenties, for example, reduction of lean body mass and higher probability to build up body fat, involving a decrease in basal energy metabolism. Reduced insulin sensitivity or elevated blood lipids are a consequence. [Barzilai et al. 2012]

Ingredients which support to maintain a healthy metabolism and body composition are on high demand, because life expectancy is continuously increasing and throughout the world 606 million persons are aged 60 or over. Europe is currently the world's major area with the highest proportions of older persons (UN Population Division).

Age related diseases such as type 2 diabetes, atherosclerosis, cardiovascular diseases, and atherosclerosis or neurodegenerative diseases are a common health concern. As the population ages, inventions slowing down the aging processes and retaining the youthful health are of particular interest.

Promoting healthy aging includes maintaining healthy body composition, healthy glucose management and lipid metabolism, cell protection and energy homeostasis in order to reduce risk factors for age related diseases. Furthermore, maintaining physical power and muscle mass makes living more comfortable during aging.

Nutrition is a key to maintain health throughout life and slows down the aging process. Functional food and dietary supplement ingredients can be an attractive option to enhance quality of life during aging by preventing age related chronic diseases.

More recent scientific studies link nutrition, in particular calorie restriction, with healthy aging. It could even be demonstrated that calorie restriction increase health span in animal studies. [Nogueiras et al. 2012] The enzyme which is discussed to be important within this process is the Sirtuin 1 (SIRT1). SIRT1 is expressed in a wide range of tissues and organs and has been detected in the liver, pancreas, heart, muscle, brain and adipose tissue. SIRT1 is activated by low cellular energy status, which is caused for example by calorie restriction or exercise. Activation of SIRT1 leads to activated metabolism, including glucose management, lipid metabolism, cell protection, energy homeostasis as well as to positive effects on cell protection. [Nogueiras et al. 2012]

Recent drug development targeting SIRT1 activation alleviates metabolic dysfunction associated with obesity or other metabolic disorders. Several pharmaceutical companies communicated that they have ongoing projects with chemical substances to develop SIRT1 agents. Most of them build on the molecular structure of reservatrol, which has been shown to have SIRT1 activity. [Barzilai et al. 2012]

Despite considerable efforts by academic researchers and pharmaceutical and food industry, the development of novel ingredients to activate SIRT1 and consequently to prevent, reduce or treat metabolic disorders during aging has been slow and did not lead to market products.

The object for the present invention was to provide novel active ingredients to activate SIRT1 and to maintain or improve healthy body composition, glucose, insulin and lipid metabolism, cell protection, energy homeostasis, and physical power and muscle mass and thereby slowing down the aging process and preventing age related chronic diseases.

SUMMARY OF THE INVENTION

The inventors surprisingly found that a composition comprising a *Mangifera* (Mango) *indica* preparation has Sirtuin 1 (SIRT1) activity playing a potent role to improve metabolism, cell protection and in slowing down the aging process and preventing age related chronic diseases.

The invention relates to a composition comprising a *Mangifera* (Mango) *indica* preparation for use as a Sirtuin 1 activating agent. The *Mangifera* (Mango) *indica* as a Sirtuin 1 activating agent may be used for preventing, treating or ameliorating Sirtuin 1 related conditions or disorders in an individual in need thereof.

The preparation according to the invention is preferably a *Mangifera* (Mango) *indica* fruit powder or *Mangifera* (Mango) *indica* fruit extract, preferably a dry extract, more preferably in form of a powder. Thus, the preparation according to the invention is preferably a *Mangifera* (Mango) *indica* fruit powder or an extract thereof, for example a water extract made from *Mangifera* (Mango) *indica* fruit powder. Preferably, the extract is dried, for example in form of a powder.

Thus, the invention relates to a novel SIRT1 agent, *Mangifera* (Mango) *indica* or a composition comprising *Mangifera* (Mango) *indica*, to improve and/or maintain a healthy body composition, to improve and/or maintain glucose or insulin management, maintaining well-aging, to improve and/or maintain a healthy lipid or fat metabolism, to prevent and/or treat overweight, for maintaining well aging, to improve and/or maintain a healthy energy homeostasis, to protect cells, to repair DNA and/or for maintaining physical power and/or muscle mass during aging. In this respect, the composition according to the invention thereby slows down the aging process and prevents age related chronic diseases. In particular, the use of the above-mentioned composition and/or preparation for the above-mentioned conditions is part of the invention.

The invention describes a novel SIRT1 agent, *Mangifera* (Mango) *indica* or a composition comprising *Mangifera* (Mango) *indica*, to reduce the risk to develop obesity, reducing risk to develop diabetes type II, reducing risk of developing elevated blood lipid levels or reducing risk of developing atherosclerosis and/or cardiovascular diseases. In particular, the above-mentioned invention relates to the composition comprising a *Mangifera* (Mango) *indica* preparation for use in preventing, treating or ameliorating the above-mentioned indications.

The invention relates to a composition comprising an active ingredient having SIRT1 activating activity. This ingredient is, preferably, a preparation comprising *Mangifera* (Mango) *indica*, more preferably a *Mangifera* (Mango) *indica* fruit powder preparation or a *Mangifera* (Mango) *indica* fruit extract.

In particular, the invention relates to a *Mangifera* (Mango) *indica* fruit preparation for use as a Sirtuin 1 activating agent for preventing, treating or ameliorating Sirtuin 1 related conditions or disorders in an individual in need thereof, preferably wherein the fruit preparation is a fruit powder.

Thus, typically the entire *Mangifera* (Mango) fruit which consists of fruit pulp and peel is used for the *Mangifera* (Mango) *indica* fruit preparation for use in accordance with the present invention. The fruit extract may be a water based sample preparation from the *Mangifera* (Mango) fruit.

In other words, the invention relates to a *Mangifera* (Mango) *indica* fruit preparation as an active ingredient and its use for treating or ameliorating SIRT1 related disorders or conditions by administering to an individual in need thereof a *Mangifera* (Mango) *indica* preparation in an amount sufficient for SIRT1 activation or in an amount sufficient to prevent, treat or ameliorate the above-mentioned diseases or conditions. The treating or ameliorating preferably comprises maintaining healthy body composition, maintaining healthy glucose or insulin metabolism, treating obesity and/or overweight, reducing risk to develop diabetes type II, maintaining well aging, maintaining a healthy fat (or lipid) metabolism, reducing risk to develop elevated blood lipid levels, reducing risk to develop atherosclerosis and/or cardiovascular diseases, protecting cells, repairing DNA and/or maintaining physical power and/or muscle mass during aging.

In addition, the invention relates to a method of activating Sirtuin 1 by administering a composition comprising *Mangifera* (Mango) *indica* preparation for an individual in need thereof. In an additional embodiment the method is an in vitro method for using *Mangifera* (Mango) *indica* as a Sirtuin 1 activating agent in cells.

In an additional embodiment, the invention relates to a method for preventing, treating and/or ameliorating Sirtuin 1 related disorders or conditions by administering to an individual in need thereof a *Mangifera* (Mango) *indica* preparation in an amount sufficient for Sirtuin 1 activation, wherein the preventing, treating and/or ameliorating comprises maintaining well aging, maintaining healthy body composition, maintaining healthy glucose or insulin metabolism, treating and/or preventing overweight and/or obesity, reducing risk to develop diabetes type II, maintaining a healthy fat (or lipid) metabolism, reducing risk to develop elevated blood lipid levels, reducing risk to develop atherosclerosis and/or cardiovascular diseases, protecting cells, repairing DNA and/or maintaining physical power and/or muscle mass during aging.

In one alternative embodiment, the invention does not concern the use of the *Mangifera* (Mango) *indica* fruit preparation in the prevention and/or treatment of conditions related to glucose or insulin management and/or to the prevention and/or treatment of diabetes.

In addition, or alternatively, in one embodiment the present invention does not concern the use of the *Mangifera* (Mango) *indica* fruit preparation in the treatment of inflammation.

According to the Example a water extract which was tested for SIRT1 activity does not comprise quercetin and/or kaempferol. Thus, the SIRT1 activity in the fruit preparation is not induced by quercetin and/or kaempferol.

In addition, or alternatively, in one embodiment of the present invention, the *Mangifera* (Mango) *indica* fruit extract does not comprise quercetin and/or kaempferol.

In a further embodiment the invention relates to a kit to activate SIRT1 for maintaining healthy body composition, maintaining well aging, maintaining healthy glucose or insulin metabolism, treating and/or preventing overweight and/or obesity, reducing risk to develop diabetes type II, maintaining a healthy fat (or lipid) metabolism, reducing risk to develop elevated blood lipid levels, improving or maintaining a healthy energy homeostasis, protecting cells and/or repairing DNA, reducing risk to develop atherosclerosis and/or cardiovascular diseases, maintaining physical power and/or muscle mass during aging comprising a *Mangifera* (Mango) *indica* preparation or a composition comprising a *Mangifera* (Mango) *indica* preparation and instructions for administration. Thus, the *Mangifera* (Mango) *indica* preparation may be packaged in a kit.

Preferably, the composition according to the invention is comprised in a food product, dietary supplement or medicament and the concentration of the active ingredient, *Mangifera* (Mango) fruit powder, is from about 1 mg up to about 10 g, preferably about 20 mg up to about 4 g and most preferably about 100 mg to about 300 mg. Alternatively, if the active ingredient is a *Mangifera* (Mango) fruit extract the applied concentration is from about 0.2 mg up to about 2000 mg, preferably about 4.5 mg up to about 910 mg and most preferably about 22 mg to about 70 mg.

The preparation may be administered preferably orally 1-2 times a day. The preparation can also be administered topically.

Furthermore, preferably, an aqueous sample preparation of Mango fruit powder having SIRT1 activity may not have an effect on alpha-glucosidase and/or alpha-amylase activity.

The composition according to the invention may, additionally, comprise a further agent capable of improving metabolism and/or cell protection. This further agent may, preferably, be a prebiotic agent, a probiotic agent, a fiber, a polysaccharide, a phytosterol, a plant extract, an antioxidant, a lipid, a phospholipid, an amino acid, a protein, a peptide, a bulking agent or a medicament. Thus, preferably, the preparation is present in a composition, wherein the composition further comprises the above-mentioned further agent.

The composition according to the invention may, additionally, comprise a further SIRT1 and/or SIRT3 activating agent preferably derived from Alliaceae, Amaryllidaceae, Apiaceae, Grossulariaceae, Juglandaceae, Moraceae, Pinaceae, or *Allium cepa, Arachis hypogaea, Capparis spinosa, Coriandrum sativum, Dalbergia odorifera, Fragaria x ananassa, Glycyrrhiza uralensis, Juglans Regia, Sclerocarya birrea, Malus domestica, Morus alba, Morus nigra, Morus rubra, Picea abies, Polygonum cuspidate* (syn. *Fallopia japonica*), *Rhus verniciflua, Ribes nigrum, Ribes rubrum, Ribes uva-crispa, Scutellaria baicalensis, Vaccinium cyanococcus, Vaccinium oxycoccos, Vaccinium vitis-idaea* or Anacardiaceae, Capparidaceae, Ericaceae, Fabaceae, Lamiaceae, Polygonaceae, Rosaceae, Verbenaceae or Vitaceae families; *Capparis spinosa, Fragaraia vesca, Fragaria x vescana, Glycyrrhiza Glabra, Vitis vinifera*; or a compound selected from butein, fisetin, isoliquiritigenin, kaempferol, myricetin, oroxylin A, Vicenin 2, piceatannol, quercetin, resveratrol or viniferin or a combination thereof. More preferred SIRT1 or SIRT3 activating agents are agents derived from Anacardiaceae, Capparidaceae, Ericaceae, Fabaceae, Lamiaceae, Polygonaceae, Rosaceae, Verbenaceae or Vitaceae families; *Capparis spinosa, Fragaraia vesca, Fragaria x vescana, Glycyrrhiza Glabra* or *Vitis vinifera*; or a compound selected from butein, fisetin, isoliquiritigenin, kaempferol, myricetin, oroxylin A, Vicenin 2, piceatannol, quercetin, resveratrol or viniferin or a combination thereof. Thus, preferably, the preparation is present in a composition, wherein the composition further comprises the above-mentioned further agent or compound.

The composition according to the invention may, additionally, comprise a further agent to support metabolism and/or cell protection, e.g. an anti-diabetic agent, a lipid reducing agent improving blood lipid profile (reducing LDL-C/TC/TG and/or increasing HDL-C), an agent reducing muscle degradation, a cell protective agent and/or an antioxidant. Such an agent may be derived preferably from Actinidiaceae, Amaryllidaceae, Apiaceae, Apiaceae, Araliaceae, Asphodeloideae, Asteraceae, Berberidaceae, Brassicaceae, Cactaceae, Caricaceae, Columelliaceae, Cucurbitaceae, Ericaceae, Fabaceae, Geraniaceae, Ginkgoaceae, Grossulariaceae, Juglandaceae, Lamiaceae, Lauraceae, Magnoliaceae, Moraceae, Musaceae, Myristicaceae Oleaceae, Pinaceae, Plantaginaceae, Poaceae, Polygonaceae, Ranunculaceae, Rosaceae, Rutaceae, Solanaceae, Theaceae, Verbenaceae, or Zingiberaceae families; *Actinidia deliciosa, Allium cepa, Aloysia tryphyla, Anacardium occidentale, Arachis hypogaea, Avena sativa, Berberis aristata, Berberis vulgaris, Brassica rapa, Bryonia dioica, Bulbine furetescens, Capparis spinosa, Capsicum annuum, Capsicum baccatum, Capsicum chinense, Capsicum frutescens, Capsicum pubescens, Carica papaya, Cinnamomum verum, Citrus paradise, Coptis chinensis, Coriandrum sativum, Crinum asiaticum, Curcuma Longa L., Dalbergia odorifera, Datisca glomerata, Desfontainia spinosa, Fragaraia vesca, Fragaria x ananassa, Fragaria x vescana, Galega officinalis, Ginkgo biloba L., Glycine max, Glycyrrhiza glabra, Glycyrrhiza uralensis, Gymnema sylvestre, Gynostemma pentaphyllum, Hydrastis canadensis, Juglans regia, Lippia citriodora, Magnolia obovata, Mahonia aquifolium, Malus domestica, Mamordica charanita, Melissa officinalis, Momordica charantia Linn, Morus alba, Morus nigra, Morus rubra, Musa x paradisiaca, Musa acuminata, Musa balbisiana, Myristica fragrans, Nigella sativa, Olea europaea, Opuntia ficus-indica, Panax ginseng, Pelagonium spp., Perilla frutescens, Petroselinum crispum, Picea abies, Plantago major, Polygonum cuspidate* (syn. *Fallopia japonica*), *Rhizoma coptidis, Rhus verniciflua, Ribes nigrum, Ribes rubrum, Ribes uva-crispa, Saussurea involucrate, Scutellaria baicalensis, Siraitia grosvenorii, Vaccinium cyanococcus, Vaccinium oxycoccos* or *Vaccinium vitis-idaea*, or a compound selected from anacardic acid, anthocyanidins, apigenin, ascorbic acid, guar gum or a combination thereof, agents derived from Anacardiaceae, Capparidaceae, Poaceae, Vitaceae, *Vitis vinifera* or *Zea mays*; or a compound selected from alpha amylase inhibitors, alpha-lipoic acid, berberine, beta-glucans, biguanides, butein, capsaicin, chitoson, chlorogenic acid, coenzymQ10, L-carnitin, creatine, crinamine, curcubitane, curcumin, damulin A and B, epigallocatechin-3-gallate, fibrates, fisetin, galegine, genistein, ginsenoside, glabridin glucomannan, glucosidase inhibitors, hispidulin, hydroxytyrosol, imino-sugars, indole-3-carbinol, inositol, inulin, isoginkgetin, isoliquiritigenin, kaempferol, momordicoside A, L-arabinose, licochalcone A, lipase inhibitors, luteolin, myricetin, nectandrin B, nootkatone, obovatol, omega-3-fatty acids, oroxylin A, phytostanol, phytosterols or their esters, piceatannol, psyllium, pyrroloquinolin quinone, quercetin, red yeast rice, resveratrol, rosmarinic acid, salicylic acid, selenium, spino side, statines, thymoquinone, tocopherol, vicenin 2 or viniferin or a combination thereof. Most preferred agents are derived from Anacardiaceae, Capparidaceae, Poaceae, Vitaceae, *Vitis vinifera* or *Zea mays*; or a compound selected from alpha amylase inhibitors, alpha-lipoic acid, berberine, beta-glucans, biguanides, butein, capsaicin, chitoson, chlorogenic acid, coenzymQ10, L-carnitin, creatine, crinamine, curcubitane, curcumin, damulin A and B, epigallocatechin-3-gallate, fibrates, fisetin, galegine, genistein, ginsenoside, glabridin glucomannan, glucosidase inhibitors, hispidulin, hydroxytyrosol, imino-sugars, indole-3-carbinol, inositol, inulin, isoginkgetin, isoliquiritigenin, kaempferol, momordicoside A, L-arabinose, licochalcone A, lipase inhibitors, luteolin, myricetin, nectandrin B, nootkatone, obovatol, omega-3-fatty acids, oroxylin A, phytostanol, phytosterols and their esters, piceatannol, psyllium, pyrroloquinolin quinone, quercetin, red yeast rice, resveratrol, rosmarinic acid, salicylic acid, selenium, spinoside, statines, thymoquinone, tocopherol, vicenin 2 or viniferin or a combination thereof. Thus, preferably, the preparation is present in a composition, wherein the composition further comprises the above-mentioned further agent or compound.

Preferably, the invention relates to a food product, dietary supplement or medicament comprising the composition according to the invention preferably as a, a candy or gummy bear, sublingual thin-films, diary product, processed fruit and/or fruit juices, snack food, beverages, beverage bases, tea, dairy product analogs selected from soy beverages, soy-based drinks, frozen desserts and/or mixes including frozen dairy desserts, mixes or processed vegetables, vegetable juices or baked goods, a powder formulation, an extract concentrate, a chewing gum, a chocolate bar, encapsulated in gelatin or in other gelling agents, tablet, diary product, cereal bar, fruit bar, energy bar, meal replacement, smoothie as well as powdered fruit flavoured beverage, fruit puree or breakfast cereals. More preferably, the invention relates to a food product, dietary supplement or medicament comprising the composition according to the invention as a powder formulation, an extract concentrate, a chewing gum, a chocolate bar, encapsulated in gelatin or in other gelling agents, tablet, diary product, cereal bar, fruit bar, energy bar, meal replacement, smoothies as well as powdered fruit, flavoured beverage, fruit puree or breakfast cereals.

The invention further relates to a process of producing a preparation of the active ingredient as defined above comprising the steps of:

a) Selection of plant raw material, preferably done by color and size of the fruit. Harvesting is done when the fruits have reached their full size, and are preferably green to yellow, most preferably greenish. Best day time for harvesting is in the morning.

b) Preparation of the raw plant material is done immediately after harvest, preferably comprising the washing of the fruits after harvest with pure water, removing the water from the whole fruits and cutting the fruits into slices followed by drying either in the sun or by drying using a flat-bed dryer, a belt dryer, a solar dryer, a hot-air cabinet or a vacuum oven dryer. Consequently, the slices are treated to reduce microbiological load resulting in total aerobic plate count to be lower than 10.000 cfu/g; yeast, mold and coliforms/enterobacteria to be lower than 100 cfu/g; *salmonella, Escherichia coli* and *Staphylococcus aureus* to be absent in 1 g. Subsequently, the slices are milled to a particle size of preferably >80% of <2 cm; more preferably to a particle size of >85% of <5 mm and most preferably >95% of <160 μm.

As mentioned above, besides a powder of the fruit an extract thereof may be prepared which alternatively besides water extraction used in the Example may include the following steps.

c) Applying an extraction process using solvent extraction at least once, preferably either with at least one alcohol, e.g. alcohols with C1 to C7, with a mixture of at least one alcohol (C1 to C7) and water, with aliphatic hydrocarbons (e.g. heptane, hexane), with ketones (e.g. acetone, methyl ethyl ketone), or with esters (e.g. ethyl acetate). Extraction may be performed at different temperatures (e.g. 20° C. to 100° C.) and/or by applying different pressures; and/or filtration techniques. Extraction is, preferably followed by concentration and/or spray drying, vacuum belt drying, roller drying, oven drying or microwave drying of the liquid extract into a powder.

d) The extract is defined by a raw material: extract ratio of 1-200:1, preferably of 2-40:1, most preferably 3-6:1.

Preferably, the preparation comprises as active ingredient the fruit powder with a daily dosage of preferably about 1 mg up to about 10 g, preferably about 20 mg up to about 4 g and most preferably 100 mg to about 300 mg.

In some cases, the preparation may comprise as active ingredient the extract with a daily dosage of about 0.2 mg up to about 2000 mg, preferably about 4.5 mg up to about 910 mg and most preferably about 22 mg to about 70 mg.

Detailed descriptions of conventional methods, such as those employed herein can be found in the literature, for example in the book "Industrial Scale Natural Products Extraction", published in 2011 by Wiley-VCH.

In the process, the raw plant material is *Mangifera* (Mango) *indica* fruit. The raw plant material is preferably prepared by washing, cutting, drying and/or milling. Extraction can be preferably done with a raw material which particle size was reduced to lower than 5 mm$^2$. The solvent may be, preferably, water, methanol, ethanol, propanol, isopropanol, ethyl acetate, hexane, acetone, chloroform or dichloromethane. Most preferably, water is used since *Mangifera* (Mango) constituents, e.g. glycosides and various phenolic acids, which have hydrophilic properties, are extracted by water more efficiently than alcohol.

Extraction can be preferably done by room temperature to up to 150° C. Extraction is more preferably carried out from 20 to 60° C. In a further preferred embodiment, heat with additional pressure can be used.

In a preferred embodiment the extraction time is 10 min to 24 hours, more preferably from 20 min to 16 hours.

In addition, the invention further relates to an active ingredient preparation obtainable by the process according to the invention. In a preferred, alternative, embodiment of the present invention, *Mangifera* (Mango) *indica* fruit preparation may be provided as a fruit powder from dried *Mangifera* (Mango) *indica* fruit. In an alternative preferred embodiment, the preparation may be obtainable by water extraction. The preparation is, preferably, used as SIRT1 activating agent and especially its beneficial effects to maintain or improve healthy body composition, glucose, insulin and lipid metabolism, energy homeostasis, cell protection, physical power, muscle mass and thereby slowing down the aging process and preventing age related chronic diseases.

BRIEF DESCRIPTION OF THE FIGURES

FIG. 1: Activation of SIRT1 enzyme by 3 different batches of aqueous *Mangifera* (Mango) fruit extracts compared to the positive control resveratrol, measured in an in vitro assay.

DETAILED DESCRIPTION OF THE INVENTION

The inventors surprisingly found that a composition comprising the active ingredient, a *Mangifera* (Mango) *indica* preparation, has SIRT1 activity playing a role to improve metabolism, cell protection and in slowing down the aging process and preventing age related chronic diseases or conditions.

In particular, the inventors surprisingly found that the composition comprising *Mangifera* (Mango) *indica* is a novel SIRT1 agent, which can be used to improve and/or maintain a healthy body composition, to improve and/or maintain glucose or insulin management, to improve and/or maintain a healthy lipid metabolism, to improve and/or main a healthy energy homeostasis, to protect cells, repair DNA and for maintaining physical power and/or muscle mass during aging.

SIRT1 activity of *Mangifera* (Mango) *indica* preparations helps to maintain and improve a healthy body composition, a healthy glucose, insulin or lipid metabolism, helps to treat and/or prevent overweight and/or obesity, helps to reduce the risk to develop diabetes type II and/or elevated blood lipid levels, to reduce risk to develop atherosclerosis and/or cardiovascular diseases, to protect cells, repair DNA, maintain physical power and/or muscle mass during aging.

Human aging is linked to structural and metabolic changes, which start already at the end twenties. For example, reduction of lean body mass and higher probability to build up body fat, involving a decrease in basal energy metabolism is common at individuals, when the age increases. Reduced insulin sensitivity or elevated blood lipids are a consequence of the latter. [Barzilai et al. 2012]

Ingredients which support maintaining a healthy metabolism and body composition are on high demand, because life expectancy is continuously increasing and throughout the world 606 million persons are aged 60 or over. Europe is currently the world's major area with the highest proportions of older persons [UN Population Division].

Age related diseases such as type 2 diabetes, atherosclerosis, cardiovascular diseases, and atherosclerosis or neurodegenerative diseases are a common health problem. Thus, as the population ages inventions slowing down the aging processes and retaining the youthful health is of particular interest.

First-line therapies for diabetes type II are substances which increase the sensitivity for insulin, so called glitazones, substances which inhibit the gluconeogeneses in the liver, e.g. biguanides, or substances which inhibit the sugar metabolism in the gut and therefore slowing down the sugar uptake to allow moderate glucose levels in the blood, like glycosidase inhibitors. First-line therapies to reduce elevated lipid levels are statines, which reduce cholesterol synthesis.

In addition, there are several food ingredients available which may have beneficial effects to maintain a healthy body composition and healthy metabolism and to prevent metabolic diseases. These ingredients are mainly only able to improve one part of the metabolism, like the glucose or the lipid metabolism. Most of them reduce the intake of sugar and fat within the gut by inhibition of enzymes which cut the nutritional compounds into bioavailable pieces; for example glycosidase inhibitors or phytosterols or fat binder. In general, it can be said that more food ingredients are available which support a healthy lipid blood level than focusing on glucose management and energy status. For example, the lipid metabolism is improved by the intake of L-carnitin, which improves lipid oxidation. In addition, substances like conjugated linoleic acid support fat metabolism and the reduction of body fat also has a beneficial effect on the generation and overall number of adipocytes, leading to an improved body composition. In addition, several blends of amino acids and/or proteins are available to support energy homeostasis and muscle mass.

Promoting healthy aging includes maintaining healthy body composition, glucose management and lipid metabolism, and energy homeostasis to reduce risk factors for age related diseases. Furthermore, maintaining physical power and muscle mass make living more comfortable during aging.

Today commercially available ingredients show isolated activities not taking the overall metabolism into account. SIRT1 agents have the advantage that they are able to beneficially influence the glucose as well as the lipid metabolism while having a positive effect on the energy level, muscle mass and cell protection. They mimic calorie reduction and therefore, physiological processes are triggered, which have been evolutionary developed for the human body. Energy homeostasis is a key aspect and the overall improvement of metabolism and cell protection leads to beneficial effects to maintain or improve healthy body composition, glucose and lipid metabolism, energy homeostasis, and physical power and muscle mass and thereby slows down the aging process and prevents age related chronic diseases.

Nutrition is a key to maintain health throughout life and slow down the aging process. Functional food and dietary supplement is an attractive option to enhance quality of life during aging by preventing age related chronic diseases. [Nogueiras et al. 2012]

The invention provides a new important possibility to maintain health throughout life, particularly to maintain a healthy metabolism and quality of life during aging by preventing age related chronic diseases not only targeting isolated symptoms of age related metabolic changes but attacking the age related metabolic and structural changes systemically.

DEFINITIONS

It is to be noted that the term "a" or "an" entity refers to one or more of that entity; for example, "a preparation", is understood to represent one or more preparations. As such, the terms "a" (or "an"), "one or more", and "at least one" can be used interchangeably herein. Unless stated otherwise, the terms "disorder" and "disease" are used interchangeably herein. By "subject" or "individual" or "animal" or "patient" or "mammal", is meant any subject, particularly a mammalian subject, e.g., a human patient, for whom diagnosis, prognosis, prevention, or therapy is desired.

"Aging" means the accumulation of changes in a person over time and involves physical, psychological, and social changes. It can be divided into different life stages. It starts with the juvenile (0-19 years) followed by the early adulthood (20-39 years), middle adulthood (40-59 years) and the late adulthood (60+ years).

"Improving/Well Aging" means to stay healthy and vital during aging process. With age the metabolism changes and the risk to develop chronic diseases such as type 2 diabetes, arthrosclerosis, cardiovascular diseases increases. High percentage of body fat and reduction of physical power as a result of the changing metabolism during the aging process reduces the quality of life. Nutrition and stress reduction is a key to maintain health throughout life and slow down the aging process.

"Elevated blood lipids" levels means that the so called "bad" lipids such as the total cholesterol and LDL (Low Density Lipoprotein) are enhanced. In dyslipidemia, TC and LDL-C are increased and the "good" lipids such as the HDL (High Density Lipoprotein) are reduced. Classification of optimal lipoprotein levels are LDL-C<100 mg/dl, total cholesterol<200 mg/dl, HDL cholesterol<40 mg/dl [National Cholesterol Education Program]. Enhancement of the LDL/HDL ratio is a well known risk factor for arthrosclerosis.

"Glucose level" is the amount of glucose present in the blood. The body naturally tightly regulates blood glucose levels as a part of metabolic homeostasis. Insulin, a hormone expressed in the b-cells of the pancreas is the key regulator of the blood glucose level. A decrease in Insulin sensitivity leads to high concentration of glucose in the blood and type 2 diabetes. Diabetes is diagnosed at fasting blood glucose of greater than or equal to 126 mg/dl. [American Diabetes Association 2000]

"Body composition" describes the percentages of fat, bone, water and muscle in human bodies. It can be measured by different ways such as the caliper method or the bioelectrical impedance analysis (BIA). A healthy woman in middle age consists of 25-31% of body fat and 29-37% muscle mass. Within the aging process the body fat content increases to 34-39% and the muscle mass decrease to 20-27% in women older than 60 years. In men older than 60 years the body fat mass increase from 16-24% to 25-30% and the body muscle mass from 35-44% to 27-34%.

"The active ingredient", is a *Mangifera* (Mango) *indica* fruit preparation.

The "Mango plant" (*Mangifera indica* L.) belongs to the Anacardiaceae (cashew or sumach) family and originates from an area between Assam in India and Myanmar. Mango is one of the most important tropical fruits which are grown worldwide. More than half of the global amount of Mango is produced in India, where more than 1000 different varieties are cultivated.

"Mango trees" are growing to a height of 3-40 m, with dense foliage and heavily branched from a stout trunk. The leaves are dark green, linear-oblong, about 25-cm long and 8-cm wide and are spirally arranged on branches. The inflorescence occurs in panicles consisting of about 3000 tiny whitish-red or yellowish-green flowers. The Mango fruits differ in size, shape, color, fiber content, flavour, taste and constituents, all depending on the variety. The fruit consists of a thick, smooth and waxy skin (exocarp), a fleshy pulp (mesocarp) and a thick, leathery and fibrous endocarp which covers many seeds (Tharanathan R N et al., 2006).

"Mango fruits" are consumed in many different stages of ripening. The green Mango fruits are utilized as pickles and chutneys or as a powder; the ripe fruits are used for many purposes such as pulp, juice, jam and many others (Tharanathan R N et al., 2006).

Several phytochemical investigations of Mango fruits revealed the presence of significant levels of bioactive compounds such as polyphenols, vitamin C, carotenoids, anthocyanin and flavonoids (Schieber A et al., 2000; Ribeiro S M R et al., 2008) and small amount of triterpenes (Scartezzini P and Speroni E, 2000).

The most dominant phenolic compounds in the Mango pulp are phenolic acids, e.g. gallic acid, ferulic acid and tannic acid (Singh U P et al., 2004; Schieber et al., 2000), various quercetin-, kaempferol- and rhamnetin-glycosides, the xanthone mangiferin occurs as well, however, in a smaller amount than in the leaves and bark (Masibo M and He Q, 2008; Ribeiro S M R et al., 2008; Berardini N et al., 2005). As shown in the examples the SIRT1 activity of the *Mangifera* fruit extract, is not induced by quercetin or kaempferol, as these molecules could not be detected in the sample preparation applied for the in vitro assay.

Different factors may influence polyphenolic concentration; one of them consists in the genetic differences between cultivars or varieties. Beside these, growing conditions, maturity, ripeness, and postharvest handling regimes may also have an influence on the polyphenolic contents. Mango polyphenolics are highest during fruit growth and decrease with ripening (Manthey J A et al., 2009; Bernardini N et al., 2005 Abdul Aziz N A et al., 2011; Kim H et al., 2010, Singh U P et al., 2004). The inventors surprisingly found a new mode of action for *Mangifera* (Mango) *indica*, in particular the activation of the enzyme SIRT1.

SIRT1 is a member of sirtuins, which includes SIRT1-7, a family of highly conserved NAD+ dependent deacetylases that act as cellular sensors to detect energy availability and metabolic processes (Nogueiras et al. 2012). SIRT1 is expressed in a wide range of tissues and organs and has been detected in the liver, pancreas heart, muscle, brain and adipose tissue. SIRT1 is activated by high NAD+ levels, a condition caused by low cellular energy status, which could be e.g. caused by calorie restriction or exercise. Activation of SIRT1 leads to the deacetylation of target proteins which are important for apoptosis, the cell cycle, circadian rhythms, mitochondrial function, and activated metabolism, including glucose management, lipid metabolism, and energy homeostasis as well as to positive effects on cell protection. Several mouse models have been used in order to investigate the metabolic function of SIRT1. It could be demonstrated that over-expression of SIRT1 show decrease in adiposity, serum cholesterol, and insulin, while displaying increased resistance to obesity-generated glucose intolerance and insulin resistance.

SIRT1 has the following proven effects linked to the beneficial effects described in this invention:

Glucose or Insulin Management:

SIRT1 has beneficial effects of glucose or insulin management in the liver, in the pancreatic beta cells and in the skeletal muscle cells.

In the liver SIRT1 is upregulated during negative energy balance, like calorie restriction, and inhibits glycolyses and stimulates gluconeogeneses by deacetylation of the transcriptional coactivator PGC1alpha. In addition, glucose metabolism is regulated by interaction between SIRT1 and FOXO transcription factors.

SIRT1 has cell protective effects on pancreatic beta cells, preventing the hyperglycemia-induced damage of these cells which produce insulin, which is necessary to regulate the glucose uptake into the cell and its metabolism. Insulin secretion itself is also stimulated by SIRT1 leading to a higher glucose tolerance of the cells. Within the muscles cells SIRT1 improves insulin sensitivity.

Lipid Metabolism:

SIRT1 has beneficial effects on lipid metabolism in the liver, the skeletal muscle and in adipocytes.

In the liver SIRT1 regulates hepatic fatty acid metabolism by activating the AMPK/LKB1 signaling pathway. Furthermore, it plays an important role in cholesterol homeostasis by deacetylation of the liver X receptor (LXR) and the critical regulator SREBP.

In the skeletal muscle SIRT1 deacetylates PGC-1a to induce mitochondrial fatty acid oxidation in a glucose-scarce environment. Furthermore, SIRT1 deacetylates and activates acetyl-CoA synthetase (AceCS), which can induce substantial fatty acid synthesis.

In the adipocytes SIRT1 favors lipolysis and fatty acid mobilization in response to fasting by repressing PPARg which is essential for adipogenesis. Another pathway involves the deacetylation of FOXO1 and stimulation of ATGL gene transcription.

Energy Homeostasis:

SIRT1 activates PGC-1$\alpha$ (peroxysome proliferator-activated receptor gamma coactivator-1$\alpha$) which directly coactivates factors relating to mitochondrial biogenesis and respiration rates as well as the uptake and utilization of substrates for energy production in different tissues (e.g. in the liver where SIRT1 controls the neogeneration of glucose by modulating PGC-1$\alpha$ and CREB (cAMP response element-binding protein) regulated transcription coactivator 2. Furthermore, activated SIRT1 results in deacetylation of PGC-1$\alpha$ in muscle and brown fat tissue and leads to an increase in its transcriptional activity which would then allow the cell to increase mitochondrial respiration and meet energy requirements when exposed to energy stress (Canto and Auwerx, 2009; Lagogue M et al., 2006).

Muscle Mass (Body Composition):

SIRT1 modulates muscle differentiation (Nogueiras et al. 2012). Furthermore, SIRT1 plays a role in deacetylation and of PGC-1a and improved mitochondrial content and fatty acid utilization (Gurd et al 2011).

Cell Protection and DNA Repair:

Substrates which are deacetylated by SIRT1 include also proteins such as p53 and transcription factors which are involved in DNA repair, e.g. Ku70, FOXLB or NBS1 (Nijmegen breakage syndrome protein). Deacetylation of these targets by SIRT1 results in reduction of stress induced apoptosis, increased DNA repair in cells after radiation exposures and cell survival by delayed cell cycle progression. By activating FOXO proteins, e.g. FOXO3a (forkhead box group) resistance to oxidative stress is increased.

A further mechanism for cell survival is autophagy, which is a cellular housekeeping process for cleansing aberrant and dysfunctional molecules and organelles. SIRT1 regulates the autophagy process via several factors, e.g. the FoxO and p53 pathways (Salminen A and Kaarniranta K (2009).

Surprisingly, the inventors of the present invention demonstrated that *Mangifera* (Mango) *indica* has SIRT1 activity.

In order to induce the SIRT1 effects the concentration of the active ingredient, *Mangifera* (Mango) fruit powder, is from about 1 mg up to about 10 g, preferably about 20 mg up to about 4 g and most preferably about 100 mg to about 300 mg. Alternatively, if the active ingredient is a Mango fruit extract which applied concentration is from about 0.2 mg up to about 2000 mg, preferably about 4.5 mg up to about 910 mg and most preferably about 22 mg to about 70 mg.

The composition according to the present invention can be comprised in a functional food product, dietary supplement or in a drug.

"A functional food product" according to this invention is understood to be a food, beverage or infant formular product, which offers, in addition, to nutritional value a health benefit, which supports and improves health and wellbeing or helps to reduce the risk to develop a disease.

"A dietary supplement product" according to this invention are food products in form of pill, tablet, capsule, powder or liquid form, which are meant to be taken by mouth, and contain substances like vitamins, minerals, foods, botanicals, amino acids and are intended to supplement the usual intake of these substances via the normal diet.

"A food product" according to this invention relates to a powder formulation, an extract concentrate, a chewing gum, a candy or gummy bear, chocolate or sublingual thin-films, encapsulated in gelatin or in other gelling agents, tablet or milk or milk product selected from diary drinks, meal replacement drinks, milk-based drinks or flavored milk as well as yoghurt cereal or granola bar, fruit bar, energy bar, meal replacement, processed fruit and or, fruit juices selected from fruit juices or smoothies as well as powdered fruit flavoured beverage, fruit puree, snack food beverages, beverage bases, breakfast cereals, tea, dairy product analogs selected from soy beverages, soy-based drinks, frozen desserts and/or mixes including frozen dairy desserts, mixes or processed vegetables, vegetable juices or baked goods.

"Preventing, treating and/or ameliorating Sirtuin 1 related disorders or conditions" comprises according to the invention e.g. maintaining well aging, maintaining healthy body composition, maintaining healthy glucose or insulin metabolism, treating and/or preventing overweight and/or obesity, reducing risk to develop diabetes type II, maintaining a healthy fat (or lipid) metabolism, reducing risk to develop elevated blood lipid levels, reducing risk to develop atherosclerosis and/or cardiovascular diseases, protecting cells, repairing DNA, maintaining physical power and/or muscle mass during aging.

"A medicament/drug/medicine" according to this invention is any substance with the potential to prevent or cure disease or enhance physical or mental welfare. If not stated otherwise the term "drug", "medicine", or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug", "medicine" or "medicament" shall include the complete formula of the preparation intended for use in either man or other animals containing one or more "agents", "ingredients", "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug", "medicine", or "medicament" at an intended target location within the body of man or other animals, e.g., at the skin, in the stomach or the intestine. The terms "agent", "compound" or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

As used herein, the terms "treat", "treatment" or "ameliorate" refer to both therapeutic treatment and prophylactic or preventative measures, wherein the object is to prevent or slow down (lessen) an undesired physiological change or disorder, such as the development of a disease, e.g. a gut disease or a cardiovascular disease. Beneficial or desired clinical results include, but are not limited to, alleviation of symptoms, diminishment of extent of disease, stabilization (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the manifestation of the condition or disorder is to be prevented.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" or "Pubmed" may be utilized, which is hosted by the National Center for Biotechnology Information and/or the National Library of Medicine at the National Institutes of Health. Further databases and web addresses, such as the virtual library "Martindale's center" are known to the person skilled in the art and can also be obtained using internet search engines.

Several documents are cited throughout the text of this specification. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way.

The practice of the present invention will employ, unless otherwise indicated, conventional techniques of plant biology, chemistry, biochemistry, physiology and pharmacology which are within the skill of the art.

Example 1

SIRT1 Assays

1. Aim

The potential activation effect on SIRT1 of aqueous extracts, applied as sample preparation, of 3 batches of Mango fruit powder was determined.

2. Material and Methods

Extraction

Three batches of dried Mango fruit powder were extracted with water for 15 min using an ultrasonic bath, the extraction was repeated once and the raw extracts were filtered. The clear extracts were concentrated in a rotation evaporator to a dry content of approximately 20%.

Samples

The samples were dissolved in water. The assay conditions for all assays are listed in the following table.

TABLE 1

Samples for SIRT1 activation assay

| Samples | Assay concentrations (µg/mL) | Solvent (final) |
|---|---|---|
| Batch 1 | 14.3, 35.7, 71.4, 143 | Assay buffer |
| Batch 2 | 14.3, 35.7, 71.4, 143 | Assay buffer |
| Batch 3 | 14.3, 35.7, 71.4, 143 | Assay buffer |

SIRT1 Assay

The assay was performed using SIRT1 Direct Fluorescent Screening Assay kit, (Cayman Chemical). In the assay resveratrol was used as a positive comparative control in the working concentration of 1 mM, or 228 µg/ml corresponding to a final assay concentration of 32.5 µg/ml.

Cayman's SIRT1 Direct Fluorescent Screening Assay Kit is fluorescence-based method for screening SIRT1 inhibitors or activators. In the first step, the substrate is incubated with human recombinant SIRT1 along with its co-substrate NAD+. Deacetylation sensitizes the substrate such that treatment with the developer in the second step releases a fluorescent product. The fluorophore is analyzed using an excitation wavelength of 350-360 nm and an emission wavelength of 450-465 nm.

The activation is calculated as % activation=(Sample−Initial Activity)/Initial Activity*100.

3. Results

All batches showed an activation of SIRT1 enzyme (FIG. 1). The activation was not dose dependent; in batch 1 highest activation was obtained with the highest tested concentration and was in a similar range as resveratrol; batches 2 and 3 showed highest activation with the second highest test concentration. The overall activation of SIRT1 by the three Mango fruit extract batches was 21.9%; comparable activation was seen with resveratrol (37.5%).

The assays were selected because in the prior art these assays were shown to be a validated method used within the resveratrol investigation as SIRT 1 agent. It is to be noted that it is important to select the right method, because the finding, that resveratrol or other sirtuin activating compounds (STACs) that can directly activate SIRT was controversially discussed in the past. In 2003, Howitz et al. demonstrated a direct SIRT1 activation by resveratrol and other small molecules (STATCs, sirtuin activating compounds; Howitz et al., 2003). The validity of these findings was challenged. The in vitro test then used to demonstrate that SIRT1 activation was based on a fluorescently labelled peptide substrate. It was claimed that the activation was dependent on the presence of the fluorophore on the substrate, without fluorophore no activation occurred. Two new studies by two independent research groups resolved this controversy. They demonstrated that small molecules can activate SIRT1 directly via an allosteric mechanism (Hubbard et al., 2013; Lakshminarasimhan et al., 2013). STACs, e.g. resveratrol, bind to the SIRT1 enzyme at a different site than the deacetylation site; subsequently the SIRT1 structure is altered in such a manner that the substrate can bind to SIRT1 and is deacetylated. Furthermore, it could be shown that deacetylation of a substrate by SIRT1 is only activated when the substrate contains large hydrophobic residues near the site of deacetylation (acetyl-lysine site) revealing a substrate specificity of SIRT1. The fluorophore of the substrate that was used in the in vitro SIRT1 activating assay is directly linked to the acetyl-lysine site and mimics, due to its hydrophobic characteristics, the natural hydrophobic residue on the substrate. Therefore, the observed activation of resveratrol in the in vitro assay applied here is comparable to the in vivo situation. This could be confirmed by comparing this type of SIRT1 activation assay with in vitro SIRT1 activation assays where natural substrates were used (Lakshminarasimhan et al., 2013).

Example 2

Phytochemical Investigation of Mango Fruit Powder

1. Aim of the Study

Mango fruit powder batches, which were used in the bioassays, were analyzed by HPLC in order to identify and quantify possible compounds.

2. Material and Methods

Extraction

Three batches of dried Mango fruit powder were extracted with water for 15 min using an ultrasonic bath, the extraction was repeated once and the raw extracts were filtered. The clear extracts were concentrated in a rotation evaporator to a dry content of approximately 20%.

Samples

The samples were dissolved in water.

TABLE 2

Samples for phytochemical investigation

| Samples | Dry matter content % | Extraction solvent |
|---|---|---|
| Batch 1 | 21.1 | water |
| Batch 2 | 20.7 | water |
| Batch 3 | 19.0 | water |

3. Results

The HPLC chromatogram of the batches revealed the presence of different, well separated compounds.

It could be shown, that the Mango fruit powder aqueous sample preparation comprises i.a. Mangiferin, gallic acids and flavonoids.

Furthermore, quercetin and kaempferol could not be detected.

TABLE 3

Content of different compounds (%) in Mango fruit powder aqueous sample preparation

| Samples | Mangiferin [%] | Gallic acid in [%] | Flavonoids* [%] |
|---|---|---|---|
| Batch 1 | 0.041 | 0.6 | 0.02 |
| Batch 2 | 0.038 | 0.8 | 0.044 |
| Batch 3 | 0.069 | 0.9 | 0.04 |

*Calculated as rutoside

4. Summary

It could be shown that i.a. quercetin and kaempferol are not present in water extracts.

Example 3

Assays to Investigate Effects on Alpha-Glucosidase and Alpha-Amylase

1. Aim of the Study

In this study such possible effect of Mango fruit powder was determined in an α-glucosidase assay in vitro.

2. Background

Alpha-glucosidase catalyzes the hydrolysis of the glycosidic linkage of disaccharides to generate sugar monomers that can be more easily taken up by the gut mucosa Inhibition of this enzyme therefore is able to reduce post-prandial rise in blood glucose.

Alpha-amylase catalyses the hydrolysis of starch to a mixture of maltose, maltotriose and dextrins. This enzyme cleaves individual glucosyl residues from alpha-linked polymers of glucose.

3. Material and Method

Samples

The following sample was used in the alpha-glucosidase assay.

| Sample | Assay concentrations (μg/mL) | Solvent (final) |
|---|---|---|
| Batch 1 | 0.25; 0.5; 1.0 mg/ml | water |

The following sample was used for the alpha-amylase assay.

| Sample | Assay concentrations (μg/mL) | Solvent (final) |
|---|---|---|
| Batch 1 | 0.25, 0.5, 1.0, 2.0 μg/ml | water |

4. Assay Performance

Alpha-Glucosidase Assay

The principle of the assay can be described as follows: α-glucosidase from *Saccharomyces cerevisiae* cleaves 4-nitrophenol from the substrate 4-nitrophenyl-α-D-glucopyranoside. 4-nitrophenol shows a yellow colour which can be detected with a photometer [1; 2].

The sample, respectively the control inhibitor acarbose, was preincubated with the enzyme solution at neutral pH and room temperature for 15 min. The reaction was started with the addition of the substrate 4 nitrophenyl-α-D-glucopyranoside. After 10 min the reaction was stopped and the absorbance was measured at λ=405 nm.

Alpha-Glucosidase Assay

Alpha-amylase inhibition was determined with the EnzChek Ultra Amylase Kit from Molecular Probes (Cat. No: E33651) according to suppliers instructions. Amylase enzyme was from *Bacillus* sp., Sigma, cat. No. A6380). In this assay, the substrate, a starch derivative labelled with a dye (DQ starch), when degraded by amylase, produces highly fluorescent fragments. The increase in fluorescent fragment is proportional to the amylase's activity. 10 mU/ml of α-amylase from *Bacillus* sp (Sigma-Aldrich) were pre-incubated with the samples for 10 mins at room temperature (rmt) before the addition of the substrate solution. Potential background effects of the samples were observed by substituting enzymes with the assay buffer. After 30 minutes of incubation in the dark at rmt, the fluorescence produced by the product was detected by a spectrophotometer (TECAN M200) using an excitation of 530 nm and emission detection of 590 nm. Duplicates were made for each sample point and the errors were given as difference from the mean. The dose related inhibition values were expressed as a percentage of the solvent controls. The IC50 values (corresponding to the sample concentration at which the inhibition level is 50%) were determined empirically with GraphPad-Prism (Version 4, GraphPad Software Inc., San Diego, Calif., USA).

5. Results

Alpha-Glucosidase

Aqueous sample preparation of Mango fruit powder showed no inhibitory effect on alpha-glucosidase.

Aqueous sample preparation of Mango fruit powder showed no relevant effect on alpha-amylase activity. With the highest concentration of 2 μg/ml an inhibition of approximately 10% was observed.

The assay functionality was proven with acarbose, an alpha-amylase inhibitor, which inhibited the alpha-amylase enzyme used in this assay with an IC50 value of 38.21 μM. This value is in a similar range as published IC50 values for acarbose (e.g. 23 μM).

6. Discussion and Conclusions

Aqueous sample preparation of Mango fruit powder showed no effect on alpha-glucosidase or alpha-amylase activities.

The assay validity was proven with the positive control Acarbose which inhibited the alpha-glucosidase with an IC50 value of 0.05 mM (32.3 μg/ml) and the alpha-amylase with an IC50 value of 0.038 mM (24.6 μg/ml).

DISCUSSION

The inventors surprisingly found that a composition comprising a *Mangifera* (Mango) *indica* fruit preparation, has Sirtuin 1 (SIRT1) activity, which has not been described for no fruits belonging to Anacardiaceae species before, in particular not for *Mangifera* (Mango) *indica*.

Some research has been carried out to investigate positive effects on metabolism of Mango leaves or Mango bark extracts targeting other mode of actions than SIRT1. However, fruits are a complete different plant organ having other biological functions than leaf and bark and therefore, show different phytochemical composition and it cannot be expected that similar activities can be found. Thus, the surprising results of the present invention are opening a wide application field as well as in therapy as in improving general condition of individuals.

It can be concluded that Mango fruit or Mango fruit extract acts as a SIRT1 activating agent that is having consequently beneficial effects to maintain or improve healthy body composition, glucose and lipid metabolism, energy homeostasis, physical power, muscle mass, cell protection and thereby slowing down the aging process and preventing age related chronic diseases.

REFERENCES

1. Barzilai N et al. The critical role of metabolic pathways in aging. Diabetes 2012, 61(6):1315-22.
2. Gurd B J et al. Does SIRT1 determine exercise-induced skeletal muscle mitochondrial biogenesis: differences between in vitro and in vivo experiments? J Appl Physiol 2012, 112(5):926-8.
3. UN population department: World Population Aging 1950-2050, http://www.un.org/esa/population/publications/worldageing 19502050/pdf/80chapterii.pdf. physiological process 4. Nogueiras R et al. Sirtuin 1 and Sirtuin 3: Physiological modulators of metabolism. Physiol Rev 2012, 92(3): 1479-1514
5. Pallauf K et al. Nutrition and healthy aging: Calorie restriction or polyphenol rich MediterrAsian Diet? Oxid Med Cell Longev 2013, 2013:707421
6. ADA supplement 1: American diabetes association: clinical practice recommendations 2000, Diabetes Care 2000, 23suppl1:S1-116
7. National cholesterol education program http://www.nhlbi.nih.gov/guidelines/cholesterol/atglance.htm
8. Tharanathan R N et al. Mango (*Mangifera indica* L.) The king of fruits. Food reviews International 2006, 22:95-123
9. Schieber A et al. Characterization of polyphenols in mango puree concentrate by HPLC with diode array and mass spectrometric detection. Innovative Food Science and Technologies 2000, 1:161-166
10. Ribeiro S M R et al. Phenolic compounds and antioxidant capacity of Brazilian mango (*Mangifera indica* L.) varieties. Food Chemistry 2008, 110:620-626
11. Scartezzini P, et al., Review on some plants of Indian traditional medicine with antioxidant activity, J Ethnopharmacol 2000, 71(1-2):23-43
12. Singh U P et al Characterization of phenolic compounds in some Indian mango cultivars. Int. J. Food Science and Nutrition 2004, 55:163-169
13. Masibo M and He Q. Major mango polyphenols and their potential significance to human health. Comprehensive reviews in food science and food safety 2008, 7:309-319
14. Berardini N et al. Screening of mango (*Mangifera indica* L.) cultivars for their contents of flavonol O- and xanthone c-glycosides, atnhocanins and pectin. J Agric Food Chem 2005, 53:1563-1570
15. Manthey J A et al. Influences of harvest date and location on the levels of b-carotene, ascorbic acid, total phenols, the in vitro antioxidant capacity and phenolic profile of five commercial varieties of mango. J Agric Food Chem 2009, 57:10825-10830
16. Abdul Aziz N A et al. Evaluation of processed green and ripe mango peel and pulp flours (*Mangifera indica* var. *Chokanan*) in terms of chemical composition, antioxidant compounds and functional properties. J Sci Food Agric 2011, 92:557-563
17. Kim H et al. Antoxodant and antiproliferative activities of mango (*Mangifera indica*). Food Chemistry 2010, 121:429-436
18. Ma X et al. Polyphenolic compounds and antioxidant properties of mango fruits. Scientiae Horticulturae 2011, 129:102-107
19. Lagogue M et al. Resveratrol improves mitochondrial function and protects against metabolic disease by activation SIRT1 and PGC-1α. Cell 2006, 127: 1109-1122
20. Carles Cantó and Johan Auwerx. PGC-1alpha, SIRT1 and AMPK, an energy sensing network that controls energy expenditure. Curr Opin Lipidol 2009, 20(2): 98-105
21. Salminen A and Kaarniranta K SIRT1: Regulation of longevity via autophagy. Cellular Signalling 2009, 21(9): 1356-60

The invention claimed is:

1. A method of preventing, treating or ameliorating Sirtuin 1 related conditions or disorders, which method comprises: administering a *Magnifera indica* fruit preparation to an individual in need thereof, wherein administering the *Magnifera indica* fruit preparation improves and/or maintains a healthy body composition, improves and/or maintains healthy glucose or insulin management, improves and/or maintains a healthy lipid metabolism, prevents and/or treats being overweight, maintains well aging, improves and/or maintains a healthy energy homeostasis, protects cells, repairs DNA and/or maintains physical power and/or muscle mass during aging in the individual, wherein the *Magnifera indica* fruit preparation is obtained from *Magnifera indica* fruit having a green to yellow color and dried directly after harvesting.

2. The method of claim 1, wherein the *Magnifera indica* fruit preparation is administered orally 1-2 times per day.

3. The method of claim 1, wherein the *Maignifera indica* fruit preparation is a fruit powder preparation and wherein a daily dosage of the fruit powder preparation is from about 1 mg up to about 10 g.

4. The method of claim 1, wherein the *Magnifera indica* fruit preparation is a fruit extract preparation and wherein the daily dosage of the fruit extract preparation is from about 0.2 mg up to about 2000 mg.

5. The method of claim 1, wherein the *Magnifera indica* fruit preparation is present in a composition, wherein the composition further comprises an additional agent activating Sirtuin 1 or Sirtuin 3.

6. The method of claim 5, wherein the further agent activating Sirtuin 1 or Sirtuin 3 is derived from Anacardiaceae, Capparidaceae, Ericaceae, Fabaceae, Lamiaceae, Polygonaceae, Rosaceae, Verbenaceae or Vitaceae families; *Capparis spinosa, Fragaraia vesca, Fragaria x vescana, Glycyrrhiza Glabra, Vitis vinifera*; or a compound selected from butein, fisetin, isoliquiritigenin, kaempferol, myricetin, oroxylin A, Vicenin 2, piceatannol, quercetin, resveratrol or viniferin or combination thereof.

7. The method of claim 1, wherein the *Magnifera indica* fruit preparation is present in a composition, wherein the composition further comprises an additional agent capable of improving metabolism and/or cell protection.

8. The method of claim 7, wherein the additional agent is selected from an anti-diabetic agent, a lipid reducing agent reducing LDL-C/TC/TG and/or an agent increasing HDL-C, an agent reducing muscle degradation, a cell protective agent, or an antioxidant.

9. The method of claim 7, wherein the additional agent is selected from a prebiotic agent, a probiotic agent, a fiber, a polysaccharide, a phytosterol, a plant extract, an antioxidant, a lipid, a phospholipid, an amino acid, a protein, a peptide, a bulking agent or a medicament or agent derived from Anacardiaceae, Capparidaceae, Poaceae, Vitaceae, *Vitis vinifera* or *Zea mays*; or a compound selected from alpha amylase inhibitors, alpha-lipoic acid, berberine, beta-glucans, biguanides, butein, capsaicin, chitoson, chlorogenic acid, coenzyme Q10, L-caritin, creatine, crinamine, curcubitane, curcumin, damulin A and B, epigallocatechin-3-gallate, fibrates, fisetin, galegine, genistein, ginsenoside, glabridin glucomannan, glucosidase inhibitors, hispidulin, hydroxytyrosol, imino-sugars, indole-3-carbinol, inositol, inulin, isoginkgetin, isoliquiritigenin, kaempferol, momordicoside A, L-arabinose, licochalcone A, lipase inhibitors, luteolin, myricetin, nectandrin B, nootkatone, obovatol, omega-3-fatty acids, oroxylin A, phytostanol, phytosterols or their esters, piceatannol, psyllium, pyrroloquinolin quinone, quercetin, red yeast rice, resveratrol, rosmarinic acid, salicylic acid, selenium, spinoside, statines, thymoquinone, tocopherol, vicenin 2 or viniferin or a combination thereof.

10. The method of claim 1, wherein the daily dosage of the fruit powder preparation is from about 20 mg up to about 4 g.

11. The method of claim 1, wherein the daily dosage of the fruit powder preparation is from about 100 mg to about 300 mg.

12. The method of claim 1, wherein the daily dosage of the extract about 4.5 mg up to about 910 mg.

13. The method of claim 1, wherein the daily dosage of the extract is from about to about 70 mg.

14. A method of activating Sirtuin 1, which method comprises:
   administering a *Mangifera indica* fruit preparation to an individual in need thereof, wherein the *Mangifera indica* fruit preparation treats or ameliorates Sirtuin 1 related conditions or disorders in the individual in need thereof, wherein the *Magnifera indica* fruit preparation is obtained from *Magnifera indica* fruit having a green to yellow color and dried directly after harvesting.

15. The method according to claim 14, wherein the *Mangifera indica* fruit preparation is packaged in a kit.

16. A method for treating and/or ameliorating Sirtuin 1 related disorders or conditions by administering to an individual in need thereof a *Mangifera indica* fruit preparation in an amount sufficient for Sirtuin 1 activation,
   wherein the treating and/or ameliorating comprises maintaining well aging, maintaining a healthy body composition, maintaining healthy glucose or insulin metabolism, improving and/or maintaining a healthy energy homeostasis, protecting cells, repairing DNA, treating overweight and/or obesity, reducing risk to develop diabetes type II, maintaining a healthy fat metabolism, reducing risk to develop elevated blood lipid levels, reducing risk to develop atherosclerosis and/or cardiovascular diseases and/or maintaining physical power and/or muscle mass during aging, wherein the *Magnifera indica* fruit preparation is obtained from *Magnifera indica* fruit having a green to yellow color and dried directly after harvesting.

17. A method of treating or ameliorating Sirtuin 1 related conditions or disorders, which method comprises:
   administering a *Mangifera indica* fruit preparation to an individual in need thereof, wherein the *Magnifera indica* fruit preparation is obtained from *Magnifera indica* fruit having a green to yellow color and dried directly after harvesting.

18. The method according to claim 17, wherein the *Mangifera indica* fruit preparation is a *Mangifera indica* fruit powder or a *Mangifera indica* fruit extract.

19. The method according to claim 18, wherein the *Mangifera indica* fruit extract is a dry extract.

20. The method of claim 17, wherein administering the *Mangifera indica* fruit preparation reduces a risk to develop obesity, a risk to develop diabetes type II, a risk of developing elevated blood lipid levels, and/or a risk of developing atherosclerosis and/or cardiovascular diseases in the individual.

21. The method according to claim 19, wherein the dry extract is in powder form.

22. The method of claim 18, wherein administering the *Mangifera indica* fruit preparation improves and/or maintains a healthy body composition, improves and/or maintains a healthy glucose level or insulin management, improves and/or maintains a healthy lipid metabolism, treats being overweight, maintains well-aging, improves and/or maintains a healthy energy homeostasis, maintains physical power and/or muscle mass during aging, and/or promotes cell protection and/or DNA repair in the individual.

23. The method of claim 17, wherein the *Mangifera indica* fruit preparation is administered orally 1-2 times per day.

24. The method of claim 17, wherein a daily dosage of the *Magnifera indica* fruit preparation is from about 1 milligrams up to about 10 grams and wherein the *Mangifera indica* fruit preparation is a *Mangifera indica* fruit powder preparation.

25. The method of claim 17, wherein a daily dosage of the *Magnifera indica* fruit preparation is from about 20 milligrams up to about 4 grams and wherein the *Mangifera indica* fruit preparation is a *Mangifera indica* fruit powder preparation.

26. The method of claim 17, wherein a daily dosage of the *Magnifera indica* fruit preparation is from about 100 milligrams up to about 300 milligrams and wherein the *Mangifera indica* fruit preparation is a *Mangifera indica* fruit powder preparation.

27. The method of claim 17, wherein a daily dosage of the *Magnifera indica* fruit preparation is from about 0.2 milligrams up to about 2000 milligrams and wherein the *Mangifera indica* fruit preparation is a *Mangifera indica* fruit extract.

28. The method of claim 17, wherein a daily dosage of the *Magnifera indica* fruit preparation is from about 4.5 milligrams up to about 910 milligrams and wherein the *Mangifera indica* fruit preparation is a *Mangiera indica* fruit extract.

29. The method of claim 17 wherein a daily dosage of the *Magnifera indica* fruit preparation is from about 22 milligrams up to about 70 milligrams and wherein the *Mangifera indica* fruit preparation is a Mangifera indica fruit extract.

30. The method of claim 17, wherein the *Magnifera indica* fruit preparation is present in a composition, and wherein the composition further comprises an additional agent, the additional agent activating Sirtuin 1 or Sirtuin 3.

31. The method of claim 30, wherein the additional agent is derived from
   Anacardiaceae, Capparidaceae, Ericaceae, Fabaceae, Lamiaceae, a Polygonaceae, Rosaceae, Verbenaceae or Vitaceae families; or
   *Capparis spinosa, Fragaria vesca, Fragaria x vescana, Glycyrrhiza glabra, Vitis vinifera*; or
   a compound selected from butein, fisetin, isoliquiritigenin, kaempferol, myricetin, oroxylin A, Vicenin 2, piceatannol, quercetin, resveratrol, viniferin or a combination thereof.

32. The method of claim 17, wherein the *Magnifera indica* fruit preparation is present in a composition, and wherein the composition further comprises an additional agent capable of improving metabolism and/or cell protection.

33. The method of claim 32, wherein the additional agent is selected from an anti-diabetic agent, a lipid reducing agent reducing LDL-C/TC/TG and/or an agent increasing HDL-C, an agent reducing muscle degradation, a cell protective agent, or an antioxidant.

34. The method of claim 32, wherein the additional agent is a prebiotic agent, a probiotic agent, a fiber, a polysaccharide, a phytosterol, a plant extract, an antioxidant, a lipid, a phospholipid, an amino acid, a protein, a peptide, a bulking agent or a medicament or agent derived from Anacardiaceae, Capparidaceae, Poaceae, Vitaceae, *Vitis vinifera* or *Zea mays*; or a compound selected from alpha amylase inhibitors, alpha-lipoic acid, berberine, beta-glucans, biguanides, butein, capsaicin, chitoson, chlorogenic acid, coenzyme Q10, L-carnitin, creatine, crinamine, curcubitane, curcumin, damulin A and B, epigallocatechin-3-gallate, fibrates, fisetin, galegine, genistein, ginsenoside, glabddin glucomannan, glucosidase inhibitors, hispidulin, hydroxytyrosol, imino-sugars, indole-3-carbinol, inositol, inulin, isoginkgetin, isoliquiritigenin, kaempferol, momordicoside A, L-arabinose, licochalcone A, lipase inhibitors, luteolin, myricetin, nectandrin B, nootkatone, obovatol, omega-3-fatty acids, oroxylin A, phytostanol, phytosterols or their esters, piceatannol, psyllium, pyrroloquinolin quinone, quercetin, red yeast rice, resveratrol, rosmarinic acid, salicylic acid, selenium, spinoside, statines, thymoquinone, tocopherol, vicenin 2 or viniferin or a combination thereof.

35. The method of claim 17, wherein the Magnifera indica fruit preparation is in a food product, a dietary supplement ora medicament.

36. The method of claim 35, wherein the food product, dietary supplement or medicament is a powder, an extract concentrate, a chewing gum, a chocolate bar, encapsulated in a gelatin or in other gelling agents, a tablet, a diary product, a cereal bar, a fruit bar, an energy bar, a meal replacement, a smoothie, a powdered fruit, a flavored beverage, a fruit puree or a breakfast cereal.

* * * * *